United States Patent [19]

Anikeev et al.

[11] 4,297,886

[45] Nov. 3, 1981

[54] ULTRASONIC FLAW DETECTOR FOR IMMERSION TESTING OF ARTICLES

[76] Inventors: Yakov F. Anikeev, ulitsa Stanichnaya, 82, kv. 2; Nikolai N. Panikov, ulitsa S. Kovalevskoi, 8, kv. 87; Viktor N. Ripny, ulitsa Pravdy, 113, kv. 20, all of Dnepropetrovsk, U.S.S.R.

[21] Appl. No.: 49,485

[22] Filed: Jun. 15, 1979

[51] Int. Cl.³ .......................................... G01N 29/04
[52] U.S. Cl. ....................................... 73/642; 73/644
[58] Field of Search ................. 73/644, 642, 620, 622, 73/629, 637, 638, 640; 310/335, 336; 367/150, 151, 152

[56] References Cited

U.S. PATENT DOCUMENTS

| | | | |
|---|---|---|---|
| 3,165,922 | 1/1965 | Worlton | 73/642 |
| 3,237,623 | 3/1966 | Gordon | 73/629 |
| 3,663,842 | 5/1972 | Miller | 73/642 |
| 3,958,559 | 5/1976 | Glenn et al. | 73/642 |
| 4,195,530 | 4/1980 | Ross et al. | 73/644 |

FOREIGN PATENT DOCUMENTS

| | | |
|---|---|---|
| 82273 | 5/1949 | U.S.S.R. |
| 136088 | 11/1961 | U.S.S.R. |
| 179076 | 3/1966 | U.S.S.R. |

OTHER PUBLICATIONS

V. V. Klyuev, *Instruments for Non-Destructive Methods of Flaw Detection in Articles,* pp. 4–16, 1976.

L. Bergman, *Ultrasonics and Its Use in Science and Engineering,* pp. 1–4, 1956.

Krautkramer GmbH Catalogue, "Finders With a Variable Viewing Angle", items 3 and 4.

*Primary Examiner*—Stephen A. Kreitman
*Attorney, Agent, or Firm*—McAulay, Fields, Fisher, Goldstein & Nissen

[57] ABSTRACT

An ultrasonic flaw detector for immersion testing of articles, comprising a focusing planoconcave lens whose concave surface is conical, a piezoelectric plate of trapezoidal shape with electrodes applied on to the surface thereof, and an ultrasonic oscillation attenuation unit, all three elements contacting each other and being arranged in the order given so that the concave surface of the focusing planoconcave lens and the piezoelectric plate have a common main symmetry plane and the directrix of the concave surface of the focusing planoconcave lens is disposed at the side of the larger base of the piezoelectric plate.

6 Claims, 5 Drawing Figures

ULTRASONIC FLAW DETECTOR FOR IMMERSION TESTING OF ARTICLES

BACKGROUND OF THE INVENTION

1. Field of the Invention

The present invention relates to checking materials and articles for defects by ultrasonic oscillations, and more particularly to an ultrasonic flaw detector for immersion testing of articles.

The invention may be used in devices intended for detecting defects in articles made from various materials. Most advantageously it can be used for non-destructive testing of thin-walled articles, for example, pipes.

2. Description of the Prior Art

Checking articles for defects by means of ultrasonic oscillations is widely known. It is also known that for generating ultrasonic oscillations in devices for detecting invisible defects use is made of the inverse piezoelectric effect (cf. USSR Inventors' Certificates, Nos. 82,273; 136,088; 179,076). These devices (flaw detectors) generally comprise piezoelectric elements having electrodes electrically connected with a source of high-frequency electric oscillations. Checking articles is effected, as a rule, by pulses, which allows the piezoelectric element to be used both for receiving ultrasonic waves reflecting from defects and for converting these waves into electric oscillations. The oscillations are analyzed with the aid of computing devices electrically connected with the piezoelectric element.

The detection efficiency of the above flaw detectors is improved by increasing the energy density of the ultrasonic oscillations applied to articles being checked for defects. To this end use is made of focusing elements permitting the sensitivity of flaw detectors to microflaws to be greatly enhanced. The ultrasonic oscillations are known to attenuate rapidly in gaseous environment and much slower in liquids. Therefore the ultrasonic flaw detectors are generally used for testing articles applying immersion method i.e. through a layer of liquid between the ultrasonic source and the article to be tested, thereby ensuring a good acoustic contact therebetween. Focusing the energy of the ultrasonic oscillations in the case of the immersion method is effected with the aid of focusing planoconcave lenses.

The construction of such flaw detectors allows application of the piezoelectric plates of a round or rectangular shape, made from quartz or piezoelectric materials, for example, lithium sulphate or barium titanate. In case a round piezoelectric plate is used the concave surface of the focusing lens is shaped spherical. In the case of a rectangular piezoelectric plate the concave surface of the focusing lens is shaped cylindrical.

The shape of the piezoelectric plate and hence of the focusing planoconcave lens is selected depending on what kind of defects are to be detected with a given flaw detector. For example, focusing planoconcave lenses with a spherical concave surface are used for detecting point defects (flaws and cavities) and defects being transverse relative to the generatrix of the pipe, whereas focusing planoconcave lenses with a cylindrical concave surface are used for detecting defects being longitudinal relative to the pipe generatrix. This is explained by the fact that the focusing planoconcave lenses with a spherical concave surface has a focal spot in the form of a point, whereas the lenses with a cylindrical concave surface has an elongated focal spot in the form of a line formed by plurality of focal points. Since articles, including pipes, may have defects being longitudinal or transverse relative to the pipe generatrix, as well as point defects, it is necessary for testing one and the same article to use in combination the focusing lenses with a spherical concave surface and lenses having a cylindrical concave surface, which complicates the construction of flaw detectors and their adjustment in the course of testing. The efficiency of the above method using focusing lenses of different shapes is relatively low because the focal spot area of the focusing lens having a spherical concave surface is small.

To use an ultrasonic flaw detector having a lens with a spherical concave surface capable of detecting transverse defects it is installed at an angle to the surface of the article being checked. For example, when used for checking pipes the flaw detector is positioned so that its acoustic line lies in a plane passing through the pipe axis at an angle relative to the generatrix of this pipe. This method is widely applied nowadays.

There are known ultrasonic flaw detectors using an immersion method for checking articles for defects as described above (cf., for example, "Pribory dlia nerasrushajustchego kontrolia materialov i izdelij, M., "Mashinostroenie", 1976 V.2, pp. 191–192, 179–183). These flaw detectors comprise a focusing planoconcave lens, a piezoelectric plate with electrodes applied onto the surface thereof and whereto are applied high frequency electric oscillations, and an ultrasonic oscillation attenuation unit, all said three elements contacting each other and being arranged in said order so that the main symmetry plane of the concave surface of the focusing planoconcave lens and that of the piezoelectric plate coincide.

However, when the above flaw detector is installed at an angle to the surface of the article being tested its focal spot deforms taking the shape of ellipse whose larger axis coincides with the directrix of the article. As a result focusing of the ultrasonic beam on the periphery of the focal spot in the direction of the larger axis of ellipse is distorted, which results in a lower sensitivity to defects in said regions of the focal spot. The lowest sensitivity of the detector is observed at the places which are more distant from the acoustic line of the detector.

SUMMARY OF THE INVENTION

The main object of the invention is to provide an ultrasonic flaw detector for immersion testing of articles, which, when installed at an angle to the article being tested, has a uniform sensitivity along the whole length of the focal spot.

Another object of the invention is to provide an ultrasonic flaw detector incorporating operational possibilities of both an ultrasonic flaw detector having a focusing planoconcave lens with a spherical concave surface and an ultrasonic flaw detector having a focusing planoconcave lens with a cylindrical concave surface.

Still another object of the invention is to improve the operational efficiency of ultrasonic flaw detectors for immersion testing of articles.

These and other objects of the invention are achieved by that in an ultrasonic flaw detector for immersion testing of articles, comprising a focusing planoconcave lens, a piezoelectric plate which is trapezoidal in form with electrodes applied onto the surface thereof and whereto high frequency electric oscillations are applied, and an ultrasonic oscillation attenuation unit, all said three elements contacting each other and being arranged in said order so that the concave surface of the planoconcave focusing lens and the piezoelectric plate have a common main symmetry plane. According to the invention, the concave surface of the focusing planoconcave lens is shaped conical and the directrix of said conical concave surface is located at the side of the larger base of the piezoelectric plate.

An ultrasonic flaw detector of such construction, when installed at an angle to the article being tested, feature a uniform sensitivity along the whole length of the focal spot, which widens the scope of operational possibilities of the flaw detector and improves the efficiency thereof.

For the purpose of phasing the focusing planoconcave lens it is advisable to construct the ultrasonic flaw detector for immersion testing of articles so that the generatrix of the conical surface of the focusing planoconcave lens lying in the common main symmetry plane would be parallel to the main symmetry axis of the piezoelectric plate.

It is expedient that the directrix of the conical concave surface of the focusing lens be an arc of circle, which will ensure a uniform sensitivity of the flaw detector along the whole length of the focal line and simplify the manufacture of the lens.

It is further expedient that the directrix of the conical concave surface of the focusing lens be an arc of an ellipse, which will improve focusing of conical surface of the lens without distorting uniform sensitivity of the flaw detector along the length of the focal line of the focusing lens.

The above mentioned objects and advantages of the present invention will be best understood by reference to the detailed description of embodiments thereof taken in conjunction with the accompanying drawings wherein:

For better understanding of the invention the components of the flaw detector shown in FIGS. 1-4 are spaced from each other.

DETAILED DESCRIPTION OF THE INVENTION

The ultrasonic flaw detector for immersion testing of articles comprises (FIG. 1) a focusing planoconcave lens 1, a piezoelectric plate 2 having electrodes applied onto the surface thereof, said electrodes being fed with high-frequency electric oscillations, and an ultrasonic oscillation attenuation unit 4. The concave surface 5 of the focusing planoconcave lens 1 and the piezoelectric plate 2 have a common main symmetry plane A.

Figures 1, 2:
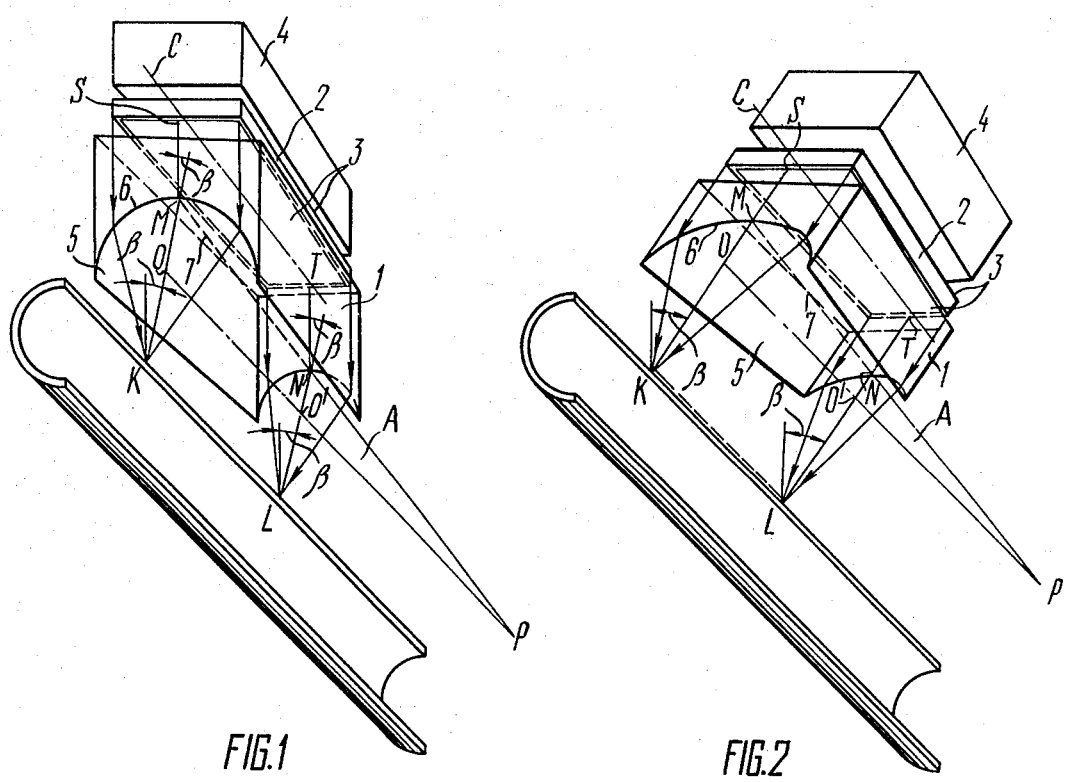
FIG. 1 is a general view of the ultrasonic flaw detector for immersion testing of articles according to the invention.
FIG. 2 schematically represents one embodiment of the ultrasonic flaw detector for immersion testing of articles, wherein according to the invention the generatrix of the conical surface of the focusing planoconcave lens, lying in the common main symmetry plane, is parallel to the symmetry axis of the piezoelectric plate.

Shown in FIGS. 1 and 2 are an axis OO'P lying in the symmetry plane A, and a generatrix MNP of the cone of a portion of the conical surface which is the concave surface of 5 of the focusing planoconcave lens 1. Lines SMK, TNL and lines with arrows show the ultrasonic beam passing from the piezoelectric plate 2 through the focusing lens 1 to the surface of the article being tested.

Angle $\beta$ (in the plane A) is an angle at which the flaw detector is installed relative to the article being tested.

Figure 3:
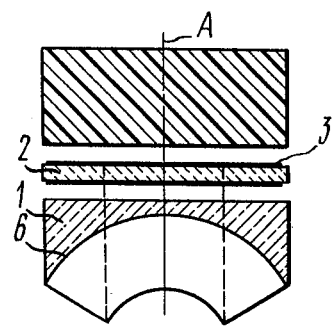
FIG. 3 is a cross-section of the flaw detector wherein the directrix of the conical concave surface of the focusing planoconcave lens is an arc of a circle.
Figure 4:
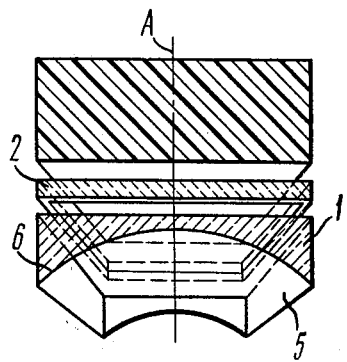
FIG. 4 is a cross-section of the flaw detector wherein the directrix of the conical concave surface of the focusing planoconcave lens is an arc of an ellipse.
Figure 5:
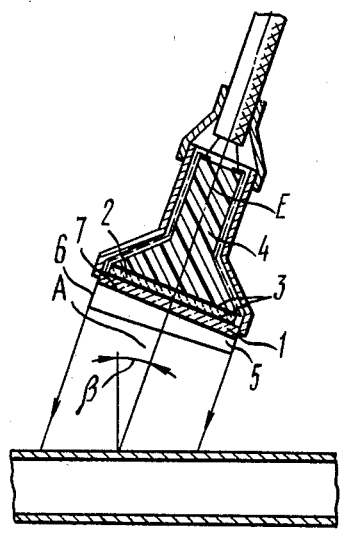
FIG. 5 is a cross-section of the ultrasonic flaw detector mounted in the body and being in the working position relative to the article being tested.

The piezoelectric plate 2 is trapezoidal. The concave surface 5 of the focusing planoconcave lens 1 is conical. The directrix 6 of the concave surface 5 is located at the side of the larger base of the piezoelectric plate 2. Shown in FIG. 1 is the ultrasonic flaw detector wherein the directrix of the concave surface of the focusing planoconcave lens 1 is an arc of circle. FIG. 2 represents the ultrasonic flaw detector wherein the directrix 6 of the concave surface 5 of the focusing planoconcave lens 1 is an arc of ellipse. As can be seen in FIG. 2, the generatrix 7 of the concave surface 5 of the focusing planoconcave lens 1, lying in the common main symmetry plane A, is parallel to the main symmetry axis C of the piezoelectric plate 2. FIGS. 3 and 4 show the ultrasonic flaw detector in cross-section, wherein is distinctly seen the shape of the concave surface 5 the directrices of which are an arc of circle and an arc of ellipse respectively. Shown in FIG. 5 is an axial elevation of one embodiment of the ultrasonic flaw detector installed in the working position relative to the article to be tested. One can seen relative positions of the flaw detector components contacting each other, namely, the piezoelectric plate 2, the focusing lens 1 and the attenuation unit 4. E is the axis of the flaw detector.

The proposed ultrasonic flaw detector for immersion testing of articles operates as follows.

The ultrasonic flaw detector is fixed in the holder of the adjusting device (not shown) so that its axis E, main symmetry plane of the lens 1 and the symmetry axis C of the piezoelectric plate 2 coincide in the plane A (FIG. 5), the portion of an article to be tested and the flaw detector being immersed in liquid, for example, water. Before testing articles a specimen is tested with the purpose of adjusting the detector, the specimen being made from the same material, having the same size and being manufactured in the same manner as the articles to be controlled. On the inner and outer surfaces of the specimen there are purposely made defects in the form of scratches, holes etc. which imitate most frequent natural transverse and longitudinal defects. Since the size and location of these defects are known, the ultrasonic flaw detector can be easily adjusted in accordance with the product quality requirements. The flaw generator is installed at an angle $\beta$ to the surface of the article to be controlled so as to excite in the article the ultrasonic oscillations of the required mode.

Angle $\beta$ is an angle between the perpendicular to the surface of the article in the focal plane (plane of the ultrasonic beam path) and the direction of the progressive ultrasonic wave from the flaw detector. Thereafter high-frequency voltage pulses from a pulse generator (not shown) are applied to the electrodes 3 of the piezoelectric plate 2, the specimen being so located that one of the immitating defects is found within the operational zone of the ultrasonic flaw detector.

Being excited the piezoelectric plate 2 begins to oscillate with the frequency equal to the pulse repetition frequency of the pulse generator and radiate ultrasonic waves (longitudinal waves) from its surfaces contacting the plane surface of the lens and the attenuation unit. The ultrasonic waves propagating towards the attenuation unit 4 quickly attenuate in the material thereof, whereas the waves propagating towards the lens 1 pass through the material thereof and the immersion fluid so that the ultrasonic beam energy is focussed in the focal plane. The distance between the piezoelectric plate and the surface of the article to be tested is determined by calculation and regulated while adjusting the flaw detector so that the signal produced in response to the ultrasonic wave reflected from the defect, has a maximum amplitude. This is achieved by moving the specimen relative to the flaw detector and simultaneously adjusting the position of the flaw detector relative to the specimen. The thin-walled articles, in the wall of which a longitudinal bending wave is excited under the action of ultrasonic oscillations, can be tested for outer and inner defects simultaneously. Testing of articles having thicker walls is effected by two flaw detectors separately, one for outer defects and the other for the inner ones. The adjustment of the flaw detector is effected so that the direction of the beam is perpendicular to the expected location of the defect i.e. the front of the ultrasonic wave propagating in the wall of the article is found on the lateral surface thereof. In case the adjustment is done for detecting both longitudinal and transverse defects, mainly in pipes, the detector after having been adjusted for transverse or point defects which is effected in the symmetry plane of the detector and the pipe, the detector is additionally adjusted for longitudinal defects. To this end the detector is moved in the cross-sectional plane of the pipe so that the angles of incidence of ultrasonic waves onto the pipe wall provides excitation of a required mode of ultrasonic oscillation propagating not along the pipe generatrix but across it. The focal line of the detector on the surface of the pipe which is a straight line having a uniform width about 1 mm (determined by the constant angle $\beta$ at which the detector is installed relative to the geratrix of the pipe and by a variable focusing distance of the lens 1 in the direction of OO'P symmetry axis) is parallel to the generatrix. At the same time there is formed an angle of incidence between the acoustic line of the detector and the perpendicular to the pipe surface in the plane of incidence, said angle lying in the cross-sectional plane of the pipe. As a result, in the diametric plane of the pipe there are detected transverse defects and in its cross-sectional plane there are detected longitudinal defects, which enhances efficiency of testing and makes it possible to simplify the testing equipment.

The proposed ultrasonic flaw detector for immersion testing of articles was used for testing thin-walled metal pipes. The detector is provided with a piezoelectric plate 2 which is 22 mm long, 0.5 mm wide and whose larger base (FIG. 5) is 9 mm, and smaller base is 6 mm. The larger radius of the concave surface 5 is 12.59 mm and the smaller one is 5.43 mm. When the detector is inclined at an angle $\beta = 36°$ to the pipe surface, the diameter of Airy's disk (width of the focal line) is 1.0 mm. The detector proved to be capable of detecting defects equivalent to the purposely made defect in the form of a hole having a diameter of 0.5 mm and a depth of 45 microns as well as in the form of a scratch 10 mm long and 20 microns deep.

The proposed ultrasonic flaw detector, when installed at an angle to the surface of the article being tested, features a uniform sensitivity along the whole length of the focal spot which widens the scope of its operational possibilities and improves its efficiency.

Various modifications may be made in the invention without departing from the spirit and scope thereof as defined in the claims.

We claim:

1. In an ultrasonic flaw detector for immersion testing of articles of the type having a focusing plane concave lens, provided with a concave surface, the focusing lens having a trapezoidal-shape, a piezoelectric plate having a symmetrical trapezoidal form with the electrodes applied to the surface thereof capable of being fed with high-frequency electric oscillations for causing the piezoelectric plate to generate ultrasonic oscillations, and an ultrasonic oscillation attenuation unit, said attenuation unit and said piezoelectric plate being placed in immediate contact with each other and said plate and said lens being placed in immediate contact with each other forming a contact plane, said focusing planoconcave lens, said piezoelectric plate and said ultrasonic altenuation unit being arranged in the aforesaid order so that the concave surface of said lens and said piezoelectric plate have a common main plane of symmetry, the improvement comprising:

said concave surface of said lens forming a conical surface, said contact plane being parellel to the genetrix of said conical surface and being in the form of a trapezoid, said lens having non-parallel side planes normal to said contact plane and being positioned on opposite sides of said concave surface with said concave surface extending arcuately therebetween, and said non-parallel sides being perpendicular to the bases of said trapezoidally-shaped lens, such that the non-parallel sides of the trapezoidally-shaped lens are formed in the same plane as the side planes of said lens normal to the said contact plane and passing through the genetrix of the conical surface equidistantly from said common main plane of symmetry, and the directrix of said conical surface being located at the side of the larger base of said trapezoid.

2. In the ultrasonic flaw detector as claimed in claim 1, wherein said piezoelectric plate has a main axis of symmetry, and wherein said genetrix of said conical surface lies in said common main plane of symmetry and is parallel to said axis of symmetry.

3. In the ultrasonic flaw detector as claimed in claim 1 or 2 wherein said directrix of said conical surface of said lens is an arc of a circle.

4. In the ultrasonic flaw detector as claimed in claim 1 or 2 wherein the directrix of said conical surface of said lens is an arc of an ellipse.

5. In an ultrasonic flaw detector as claimed in claim 1 or 2, wherein the contact plane of the focusing plano-concave lens facing the piezoelectric plate is parallel to the generating line of the conical surface and is trapezoidally-shaped.

6. In an ultrasonic flaw detector as claimed in claim 1 or 2, wherein the concave surface of said focusing planoconcave lens is a portion of a frustum of a cone.

* * * * *